United States Patent [19]

Schwanbom et al.

[11] 4,265,237
[45] May 5, 1981

[54] APPARATUS FOR ENHANCING A PERSON'S BREATHING AND/OR ARTIFICIAL RESPIRATION

[75] Inventors: Erik Schwanbom, Luebeck; Detlef Warnow, Gross Gronau, both of Fed. Rep. of Germany

[73] Assignee: Drägerwerk Aktiengesellschaft, Fed. Rep. of Germany

[21] Appl. No.: 51,143

[22] Filed: Jun. 22, 1979

[51] Int. Cl.³ .............................................. A61M 16/00
[52] U.S. Cl. ........................... 128/204.24; 128/204.25; 128/205.24
[58] Field of Search ...................... 128/204.24, 204.25, 128/204.21, 204.23, 205.11, 204.18, 205.24, 204.22, 200.21

[56] References Cited

U.S. PATENT DOCUMENTS

| | | | |
|---|---|---|---|
| 3,848,591 | 11/1974 | Smythe et al. | 128/204.23 |
| 3,889,669 | 6/1975 | Weigl | 128/204.18 |
| 3,981,301 | 9/1976 | Warnow et al. | 128/204.24 |
| 3,993,059 | 11/1976 | Sjostrand | 128/205.13 |
| 4,030,492 | 6/1977 | Simbruner | 128/200.21 |
| 4,057,059 | 11/1977 | Reid, Jr. et al. | 128/204.24 |

Primary Examiner—Henry J. Recla
Attorney, Agent, or Firm—McGlew and Tuttle

[57] ABSTRACT

An apparatus for enhancing a person's breathing and artificial respiration which includes inspiration and expiration phases and operates in a situation where the inspiration phase is repeated periodically within the time content of the operation of the lungs. A respiratory gas breathing line having a tubular connection to a person's trachea also has a connection to a gas supply line. A pressure sensor is located in the tubular connection and it is connected to pressure control means which is also connected to the tubular connection and to the gas supply. In addition, pressure sensor is located in the tubular connection and connected to pressure control means connected between the respiratory breathing line and the gas supply. A pressure reducer, a dosing valve and an inspiration valve are located in series in the connection between the gas supply and the tubular connection. The pressure control means includes a frequency control device having a housing with a control chamber therein which is separated by adjustable partition means into an inspiration control chamber and an expiration control chamber which may be adjusted in size relatively. A frequency valve is provided with an inspiration line connection to the inspiration chamber and an expiration line connected to the expiration chamber. Pneumatic inspiration control elements are located in the inspiration line and the expiration line and a second inspiration line and respiration line is connected from the respective inspiration and respiration chambers to the inspiration valve in order to open and close the valve in accordance with the setting of the control system.

6 Claims, 3 Drawing Figures

APPARATUS FOR ENHANCING A PERSON'S BREATHING AND/OR ARTIFICIAL RESPIRATION

BACKGROUND OF THE INVENTION

1. Field of the Invention

This invention relates in general to respiratory systems and in particular to a new and useful device for enhancing breathing and artificial respiration wherein the inspiration phases are repeated periodically several to many times within the time constant of the lungs and a respiratory gas supply is controlled by pressure which is sensed in a connection to the trachea.

2. Description of the Prior Art

The known respirators are controlled according to the breathing rhythm, whereby the respiration frequency can range from 1 to 70/min. The apparatus according to the invention will enhance or replace the breathing by the supply of respiratory gas to the lungs with respiration frequencies which can be substantially higher than the breathing frequency, using respiration frequencies of up to 600/min with timing ratios of inspiration time to expiration time of 3:1 to 1:5. These are achieved by pneumatic controls composed of static-logic control elements.

A respirator controlled by fluidic elements is known, where the respiration is supplied with inspiration phases repeated periodically several to many times within the time constant of the lungs. The inspiration phases are controlled over timing relays; the pressure switch, controlled by the pressure in the trachea, can end the inspiration phase after attaining a set maximum pressure, and switch to expiration.

This known apparatus uses pneumatic wall jet elements which have a high gas consumption. The respiration frequencies cannot be set directly; they must be computed over the separately set inspiration and expiration time. (Klain M, Smith RR: Fluidic Technology, Anaesthesia, 31:750, 1976).

An apparatus for enhancing breathing and/or artificial respiration is known which consists of a chamber to be set under excess pressure, to which is connected a tracheal tube. This chamber is set under excess pressure over a blow-in tube connected to the respiratory gas supply. The respiratory gas is supplied through a jet pipe arranged on the inner wall parallel to the tube axis. The chamber has an opening to the outside opposite the connection of the tracheal tube. This opening is closed by the injector effect of the blow-in tube.

The respiratory gas supplied through the jet pipe is supplied in the breathing rhythm by a control device equipped with fluidic elements. The pressure-dependence is achieved over a sensor line which is connected in a distance behind the blow-in opening of the jet pipe.

The fluidic elements used in the control device cause a high gas consumption (DOS 26 03 063). The object of the invention is to provide a respiration control with a low gas consumption adapted to the apparatus. The respiration frequency is to be set directly with a setting element without changing the timing ratio inspiration/expiration.

SUMMARY OF THE INVENTION

In accordance with the invention an apparatus for enhancing a person's breathing and artificial respiration which includes inspiration and expiration phases and an inspiration phase which is repeated periodically within the time constant of the operation of the lungs comprises a respiratory gas breathing line having a tubular connection to the person's trachea and a connection to a gas supply line. A pressure sensor is located in the tubular connection and pressure control means are connected the sensor and to a frequency valve to open and close the valve in accordance with selected pressure sensing conditions and in accordance with inspiration and respiration conditions which are sensed in respective inspiration and respiration chambers of a control chamber.

The advantages achieved by this solution permit a time-controlled supply of respiratory gas in the desired respiration rhythm. The amount of gas can be regulated at will by means of the dosing valve without disturbing the respiration rhythm. Inversely it is possible to set the respiration frequency with a setting element without changing the respiratory gas volume and without disturbing the timing ratio inspiration/expiration. The pneumatic signal from a comparison of the gas pressure taken in the tracheal tube, hence practically in the respiration path, with an adjustable limiting pressure opens the connection between the frequency control device and an inspiration valve over the pressure control. This way excess pressure, which is undesirable for the lungs, is prevented in a simple manner. The frequency control device switches automatically to expiration so that the respiratory gas continues to flow normally.

The pressure indicator, the breathing pressure mean value indicator, and the pressure-time alarm, likewise connected to the pressure sensor line, serve to ensure the safety of operation in an adequate manner.

The check valve in the excess pressure chamber presents venturi-effects, which could interfere with a more accurate and reproducible adjustment of the composition of the respiratory gas.

Accordingly it is an object of the invention to provide an apparatus for enhancing a person's breathing and artificial respiration which comprises a respiratory gas breathing line having a tubular connection to a person's trachea and a connection to a gas supply line and which includes a pressure sensor in the trachea connection which is connected to pressure control means and to an inspiration valve in a connection line which also includes a pressure reducer and a dosing valve wherein the opening and closing of the inspiration valve is effected by a frequency control device.

A further object of the invention is to provide an apparatus for enhancing a person's breathing and/or artificial respiration which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
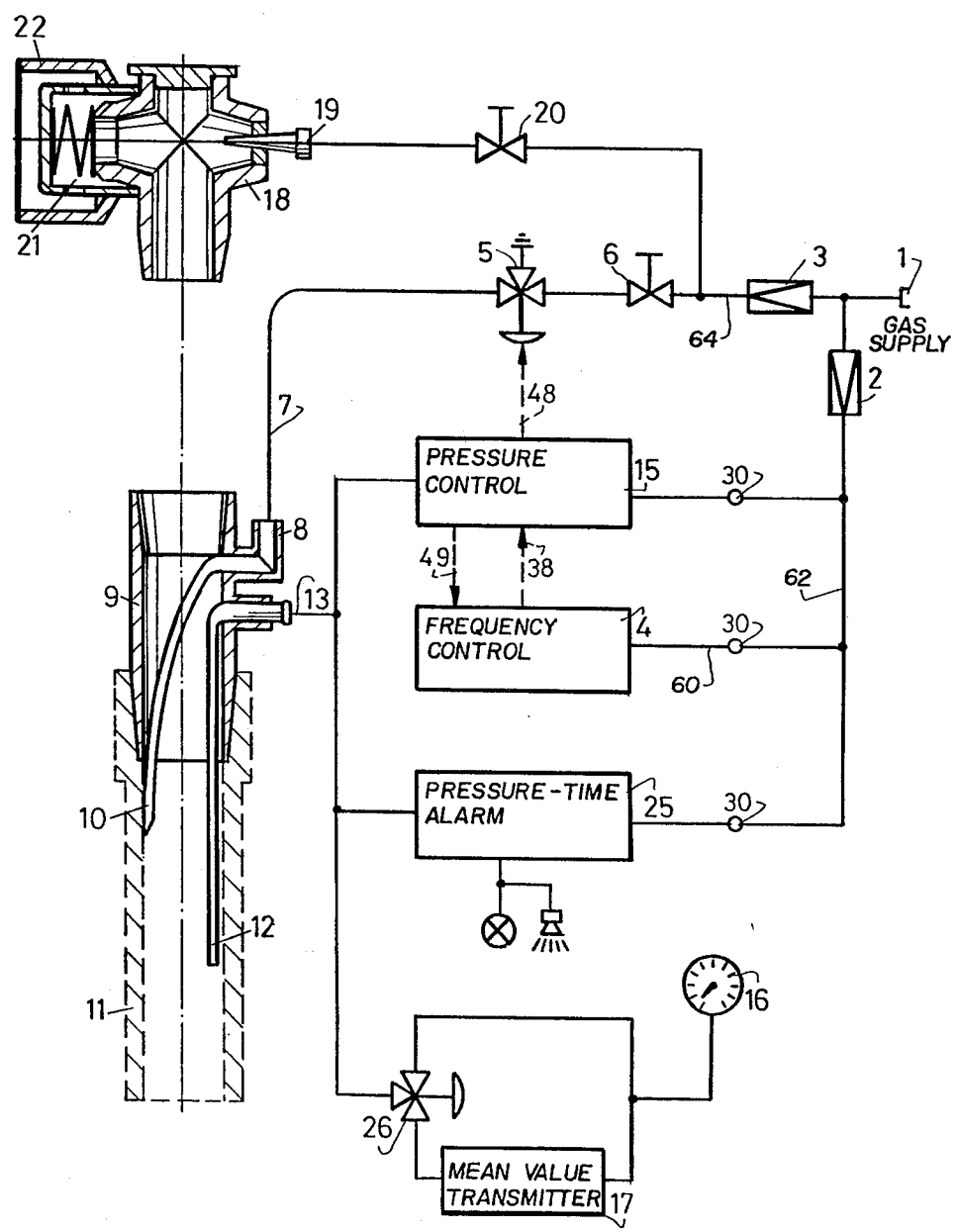
FIG. 1 is a schematic view partly in section of an apparatus for enhancing breathing and/or artificial respiration for newborn and premature babies constructed in accordance with the invention.

Referring to the drawings in particular, the invention embodied therein, comprises, an apparatus for enhancing a person's breathing and artificial respiration which has inspiration and respiration phases and where the inspiration phase is repeated periodically within the time constant of the operation of the lungs. The apparatus includes a respiratory gas breathing line 9 having a tubular portion which fits into a person's trachea tube 11. The tubular connection to the trachea of the breathing line is connected to a gas supply 1 and the gas supply is delivered through a connection 8 into the tubular connection 9 and the trachea 11 under the influence of a pressure and frequency control system.

The respirator is fed from a respiratory gas source or supply 1. The pressure of the respiratory gas is at least 1.5 bar. The connection to the respiratory gas source 1 is effected over pressure reducers 2 and 3. Over pressure reducer 3 is connected to direct respiratory gas line and over pressure reducer 2 a pressure control 15 and frequency control device 4. In the respiratory gas line behind pressure reducer 3 is arranged an inspiration valve 5, which opens and closes corresponding to the pneumatic signals from frequency control device 4. Ahead of inspiration valve 5 is arranged an adjustable dosing valve 6 with which the volume of the flowing respiratory gas can be adjusted. The respiratory gas arrives behind dosing valve 6 through line 7 in the part 8 introduced into the patient. It enters there with a pressure of 0.2 to 2.7 bar.

Part 8 has a tube 9 with axial conical connections. Into tube 9 opens a gas jet tube 10 having a blow-in opening at the bottom thereof, which is connected to line 7. Gas jet tube 10 is arranged substantially parallel to the axis of a blow-out opening on the inner wall in tracheal tube 11. The depth of immersion and thus the position of the blow-in opening is adjustable.

About 20 mm below the blow-in opening of gas jet tube 10 or lower is the opening of pressure sensor line 12, which scans the respiratory tract pressure. At this point the respiratory path pressure is not influenced by the injector effect of the respiratory gas jet issuing from gas jet tube 10. The respiratory tract pressure is fed to the pressure control 15 through signal line 13. Pressure control 15 compares the respiratory path tract pressure with an adjustable limiting pressure. If the selected limiting pressure is attained or exceeded in the comparison, indicating too much pressure has been supplied, pressure control 15 produces a pneumatic signal which opens or blocks the connection between frequency control device 4 and inspiration valve 5. Due to the resulting ventilation, the logic signal "zero" is formed, with which inspiration valve 5 is closed. This ends thus the inspiration phase immediately. The pneumatic signal from pressure control 15 also influences the switching elements in frequency control device 4, so that the latter switches to expiration.

Figure 3:
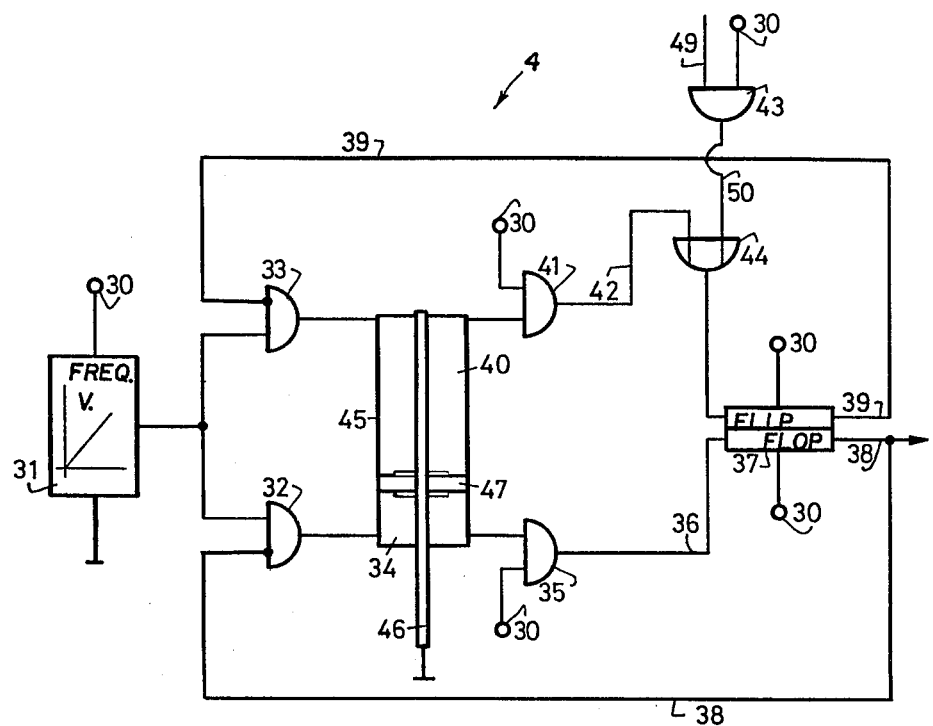
FIG. 3 is a schematic representation of the frequency control device for the apparatus shown in FIGS. 1 and 2.

The details of the frequency control device 4 with a connection linkage 38 to pressure control 15 is shown in FIG. 3. The control gas supply of all elements is effected from the pressure reducer 2 and is represented as connections 30. Volume-dosed control gas arrives from frequency valve 31 in NAND-elements 32 and 33 designed as diaphragm control elements, of which only one is controlled-through. During the expiration phase the NAND-element 32 is open and NAND-element 33 is closed. Control gas flows over NAND-element 32 in its opening phase into expiration chamber 34. It forms together with inspiration chamber 40 the control chamber 45. Inspiration chamber 40 and expiration chamber 34 are mutually adjustable in their volume by a partition 47 which can be displaced by a shifting mechanism 46. Corresponding to the time constant tau-1 from the pneumatic resistance R of frequency valve 31 and the pneumatic capacitance C1 of expiration chamber 34 the pressure rises steadily in expiration chamber 34 and identity element 35 connected with it. When the pressure attains a switching level, identity element 35 is so switched that control gas flows from connection 30 over line 36 to bistable flipflop 37, and switches the latter so that connection 30 is connected to line 38. Line 38 is thus filled with control gas. Inspiration valve 5 is switched to inspiration by the pressure line 38 over pressure control 15 and line 48 (FIG. 1), hence opened. At the same time the passage of NAND-element 32 is closed through line 38, and expiration chamber 34 is vented over NAND-element 32. The advanced control from connection 30 to line 39 is interrupted by the internal wiring of flipflop 37, and line 39 is thus made pressure-less. NAND-element 33 thus controls through that is, the amount of control gas dosed by frequency valve 31 flows now over NAND-element 33 into inspiration chamber 40. According to the time constant tau-2=R.C2 (with C2 as the pneumatic capacitance of inspiration chamber 40), the pressure rises now in inspiration chamber 40. When the switching level is reached, identity element 41 is so switched that control gas flows from connection 30 of identity element 41 through line 42 and OR-element 44 to flipflop 37, leading to the switching of flipflop 37. The expiration phase begins. Line 39 is now admitted with pressure and closes the passage in NAND-element 33. Inspiration chamber 40 is thus vented over NAND element 33. Line 39 is made pressure-less over the internal wiring of flipflop 37 and NAND-element 33 is closed. The above described cycle thus starts again.

When the respiratory tract pressure attains the limiting pressure, there is a switch to expiration over pressure control 15. The pneumatic signal formed in pressure control 15, which also effects the venting of line 48 to inspiration valve 5, leads according to FIG. 3 over line 49 to the advanced control of AND-element 43, whose output signal arrives over line 50 and OR-element 44 in flipflop 37 and switches the latter to expiration.

The charging time of expiration chamber 34 thus determines the length of the expiration t-exp., the charging time of inspiration chamber 40 determines the length of the inspiration time t-in. The sume of t-in+t-exp. equals T. If partition 47 of control chamber 45 is displaced by means of shifting mechanism 46 only the partial times t-in and t-exp. are changed, but not the total time T. Since the reciprocal value of T equals the respiration frequency f, different respiration time ratios t-in:t-exp. do not change the respiration frequency. A variation frequency f is achieved when the amount of control gas is varied on frequency valve 31. A larger volume results in a faster filling of inspiration chamber 40 and expiration chamber 34 respectively and thus in a shorter time T. Corresponding to the relation f=1/T, a shorter time T means a higher respiration frequency f. Since a varied amount of control gas does not change the ratio of the filling time of chambers 40 and 34, that is of t-inspiration to t-expiration the breathing time remains constant in a variation of the respiration frequency.

The respiratory tract pressure is indicated in pressure indicator 16. With high breathing frequencies, the respiratory pressure is indicated over a mean value-transmitter 17 after switching by three-way valve 26. In order to recognize cloggings or separations of lines, a pressure-time alarm 25 is provided, in which the respiratory tract pressure must have attained, or exceeded a certain value within a maximum period. If this value is not attained within this period, an alarm signal is released. The exceeding of the pressure level can also be used to indicate the set respiration parameters frequency and the inspiration:expiration ratio.

In order to permit spontaneous breathing, even with a high means breathing pressure, tube 9 is provided with a blow-in tube 19 which is directed into excess pressure chamber 18. Chamber 18 is connected to tube 9 and is used with tube 19 so that the pressure increase in the apparatus is achieved. To this end the amount and the pressure of the gas current through blow-in tube 19 are set with PEEP control valve 20. The PEEP values are variable between 1 and 15 mbar.

In order to prevent venturi-effects, which could disturb a more accurate and reproducible maintenance of the mixtures in the respiratory gas, a check valve 21 is arranged in a right angle to the axis of tracheal tube 11. It has a collecting vessel 22 for the expiration gas.

Figure 2:
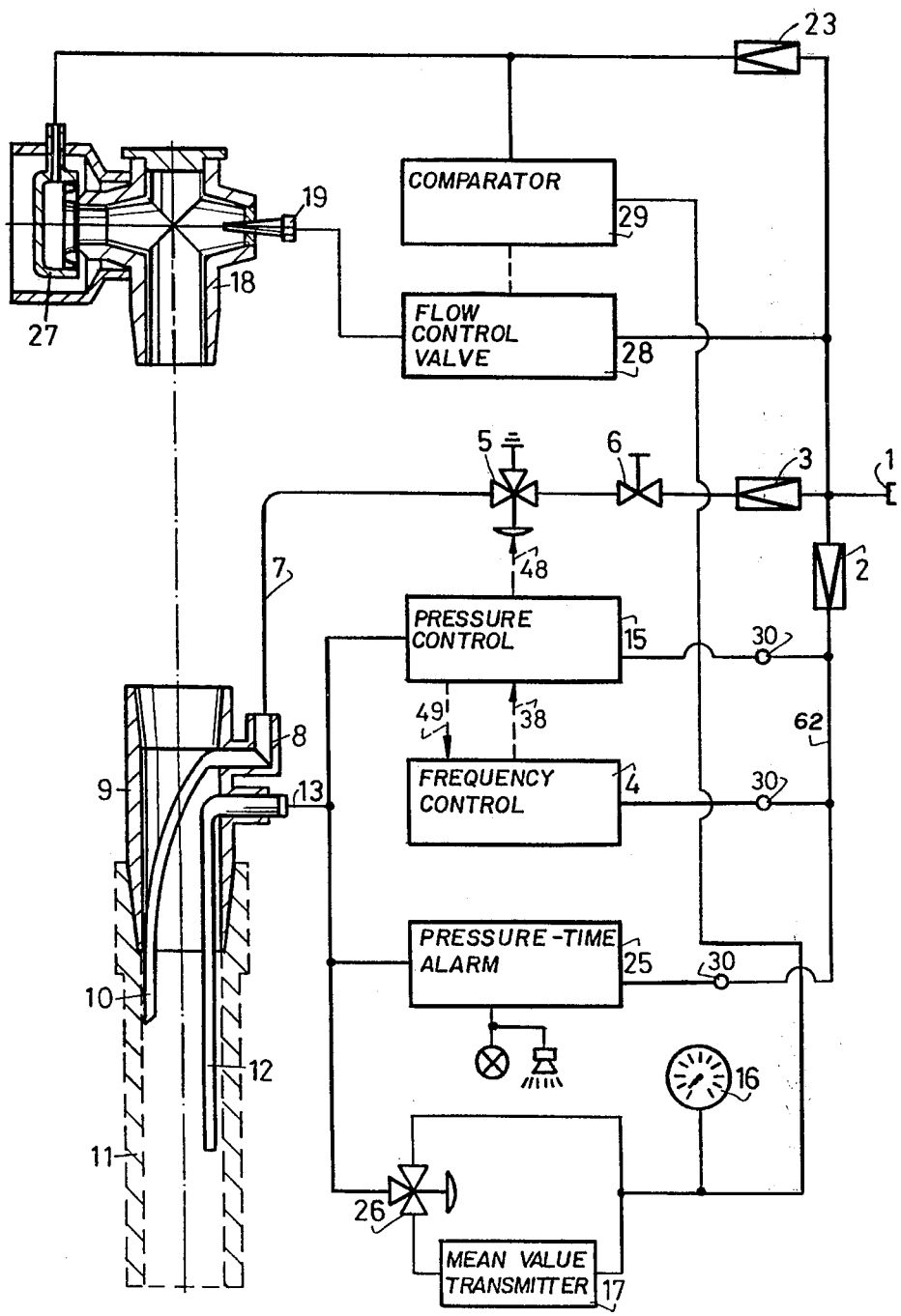
FIG. 2 is a view of a device similar to FIG. 1 provided for breathing and artificial respiration of adults.

In order to be able to use the apparatus for respiration for adults, excess pressure chamber 18 is provided with a diaphragm valve 27 whose seat is arranged perpendicularly to the axis of tube 9 as shown in FIG. 2. The control side of diaphragm valve 27 is admitted with the mean respiration pressure which can be adjusted by means of a pressure reducer 23 to control the excess pressure in chamber 18. After comparison of the existing mean pressure in the respiratory tract (from line 50) with the mean respiration pressure (from supply 1 and reducer 23) in a comparator 29, the difference of the two pressures forms the basis for the regulation of the flow control valve 28 which is connected to comparator 29. The amount of respiratory gas required for the respective case is thus fed to the patient over flow control valve 28. This is done over blow-in tube 19 and excess pressure chamber 18.

While specific embodiments of the invention have been shown and described in detail to illustrate the application of the principles of the invention, it will be understood that the invention may be embodied otherwise without departing from such principles.

What is claimed is:

1. An apparatus for enhancing a person's breathing and artificial respiration which has inspiration and expiration phases and where the inspiration phase is repeated periodically within a time constant of the operation of a person's lungs, comprising: a respiratory gas breathing line having a tubular connection adapted to be connected to a person's trachea, a blow-in line located in said tubular connection, a gas supply line connected into said tubular connection through said blow-in line in said tubular connection, a pressure sensor located in said tubular connection downstream of said blow-in line, pressure control means connected to said pressure sensor, a pressure reducer, a dosing valve, and an inspiration valve having an open and closed position all located in series in said gas supply line, said pressure control means connected to said inspiration valve and being responsive to said pressure sensor for closing said inspiration valve, frequency control means connected to said pressure control means for supplying pressure signals indicative of inspiration and expiration to said pressure control means, said pressure control means being responsive to said signals for alternately opening and closing said inspiration valve during inspiration and expiration phases, respectively, said frequency control means having a housing with a control chamber defined therein, adjustable partition means in said control chamber dividing said control chamber into an inspiration chamber portion and an expiration chamber portion of adjustable relative size, a frequency valve having an inspiration line connected to said inspiration chamber and an expiration line connected to said expiration chamber, first pneumatic diaphragm control elements in said inspiration line and said expiration line respectively, a second inspiration line connected from said inspiration chamber to said inspiration valve and a second expiration line connected from said expiration chamber to said inspiration valve, second pneumatic diaphragm control elements in said second inspiration and second expiration lines respectively, connected to said pressure control means and to said first pneumatic diaphragm control elements, said first pneumatic diaphragm control elements being responsive to said frequency control valve and signals from said second pneumatic diaphragm control elements to initiate inspiration and expiration phases, said second pneumatic diaphragm control elements producing signals at the end of inspiration and expiration phases, respectively, said pressure control means switching said second pneumatic diaphragm control elements to initiate an expiration phase and to close said inspiration valve if pressure in said tubular connection attains a selected limit.

2. An apparatus according to claim 1 including a pressure indication connected to said pressure sensor line.

3. An apparatus according to claim 1 particularly for adults wherein the amount of respiratory gas is supplied to a flow control valve, said flow control valve being controlled by the difference from the means respiratory track pressure sensed by said pressure sensor and the adjustable mean respiration pressure, said breathing line connection including the tubular portion defining an excess pressure chamber having a diaphragm valve connected to said pressure sensor for opening and closing in accordance with a predetermined pressure therein.

4. An apparatus according to claim 3 wherein said flow control valve is operated by a difference in pressure from the respiratory track pressure and the adjustable mean respiration pressure.

5. An apparatus according to claim 1, including a pressure time alarm connected to said pressure sensor line to indicate a lack of sufficient pressure in said tubular connection for a selected duration of time.

6. An apparatus according to claim 1, particularly for newborn and premature babies wherein said respiratory gas line includes a tubular portion defining an excess pressure chamber, a check valve associated with said excess pressure chamber disposed at a right angle to the axis of the connecting tube to the trachea to vent excess pressure in said excess pressure chamber and a PEEP valve connected between said gas supply line and said excess pressure chamber for supplying gas under pressure to said excess pressure chamber.

* * * * *